US012419597B1

(12) United States Patent
Litzenberger

(10) Patent No.: US 12,419,597 B1
(45) Date of Patent: Sep. 23, 2025

(54) COMPACT MECHANISM FOR ADJUSTING SOURCE TO DETECTOR DISTANCE ON C-ARM

(71) Applicant: CARESTREAM HEALTH, INC., Rochester, NY (US)

(72) Inventor: Michael A. Litzenberger, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 258 days.

(21) Appl. No.: 18/329,750

(22) Filed: Jun. 6, 2023

Related U.S. Application Data

(60) Provisional application No. 63/349,686, filed on Jun. 7, 2022.

(51) Int. Cl.
*A61B 6/00* (2024.01)

(52) U.S. Cl.
CPC .......... *A61B 6/4452* (2013.01); *A61B 6/4441* (2013.01)

(58) Field of Classification Search
CPC ..... A61B 6/4476; A61B 6/505; A61B 6/4441; A61B 6/587; A61B 6/4405; A61B 6/5241; A61B 6/54; A61B 6/4482; A61B 6/4429; A61B 6/547; A61B 6/4452; A61B 6/0487; A61B 6/4464; A61B 6/4021; A61B 6/4411; A61B 6/4447; A61B 6/032; A61B 6/035; A61B 6/4085; A61B 6/485; A61B 6/56; A61B 34/30; A61B 6/0407; A61B 2090/376; A61B 2090/3762; A61B 6/0457; A61B 5/1114; A61B 5/6802; A61B 6/102; A61B 2562/0257; A61B 5/055; A61B 5/704; A61B 6/04; A61B 6/4435; A61B 6/027; A61B 46/10; A61B 34/10; A61B 34/76; A61B 34/70; A61B 34/32; A61B 34/20; A61B 17/025; A61B 17/1671; A61B 17/7083; A61B 17/7082; A61B 2090/064; A61B 17/1626; A61B 2017/00477; A61B 2034/107; A61B 2090/031; A61B 2017/00026; A61B 2017/564; A61B 2034/108; A61B 2090/066; A61B 2017/0256; A61B 6/4233; A61B 6/4225; A61B 6/4291; A61B 6/4458; A61B 6/08; A61B 6/583; A61B 6/482; A61B 6/4423; G01N 23/083; G01N 23/087; G01N 23/04; G01N 2223/308; G01N 2223/301; G01N 2223/3303; G01N 23/046; G01N 23/185;

(Continued)

(56) References Cited

U.S. PATENT DOCUMENTS 2,933,198 A * 4/1960 Firestone ............... A61B 6/102
212/319
5,086,447 A * 2/1992 Siczek ................. A61B 6/4464
378/197

(Continued)

FOREIGN PATENT DOCUMENTS

EP 3610795 A1 * 2/2020 ............. A61B 6/032

*Primary Examiner* — Irakli Kiknadze
(74) *Attorney, Agent, or Firm* — Eugene I Shkurko

(57) ABSTRACT

A radiographic C-arm system uses a scissor extender assembly to retract and extend a detector in relation to an x-ray source of the C-arm system. The scissor extender assembly is attached to the C-arm near one end of the C-arm. The assembly comprises pivoting arms for extending and retracting the detector away from and toward the x-ray source.

8 Claims, 2 Drawing Sheets

(58) Field of Classification Search
CPC .. G01N 2223/627; G01N 23/18; H05G 1/025;
H03K 17/955; H03K 2017/9602; B60B
33/066; G01R 33/4812; B66F 7/065;
B66F 7/08; B66F 7/0625; A61G 13/10;
A61G 13/00; A61G 2203/10; A61G
2210/10; G01M 17/028
USPC ........................................................ 378/197
See application file for complete search history.

(56) References Cited

U.S. PATENT DOCUMENTS

| | | | | |
|---|---|---|---|---|
| 9,193,573 | B1* | 11/2015 | Troy ...................... | B66F 7/065 |
| 2010/0303207 | A1* | 12/2010 | Tsujii ................... | A61B 6/4405 |
| | | | | 378/197 |
| 2021/0259653 | A1* | 8/2021 | Yesudhas ............. | A61B 6/4452 |

\* cited by examiner

COMPACT MECHANISM FOR ADJUSTING SOURCE TO DETECTOR DISTANCE ON C-ARM

CROSS REFERENCE TO RELATED APPLICATIONS

This application claims priority to U.S. Patent Application Ser. No. 63/349,686, filed Jun. 7, 2022, in the name of Litzenberger, and entitled COMPACT MECHANISM FOR ADJUSTING SID ON PORTABLE C-ARM, which is hereby incorporated by reference herein in its entirety.

This application is related in certain respects to U.S. patent application Ser. No. 18/192,190, filed Mar. 29, 2023, in the name of Litzenberger et al., and entitled PORTABLE C-ARM WITH INTERCHANGEABLE DETECTORS AND WORKING AREA LIGHTING, which is hereby incorporated by reference herein in its entirety.

BACKGROUND OF THE INVENTION

The subject matter disclosed herein relates to C-arm x-ray systems. In particular, to C-arm x-ray systems having a movable detector to allow the detector to be moved closer to, or farther from, the x-ray source during, and in preparation for, a radiographic exam.

Currently, many C-arm x-ray units are sold with a detector either permanently fixed in position relative to the C-arm or attached to the C-arm with a telescoping assembly that is enabled to retract and extend the detector. As is well known to those skilled in the art, different types of detectors may include, for example, Cesium Iodide (CsI) or Gadolinium Oxysulfate (GdOS or GOS) which exhibit different sensitivities to x-rays. On most existing C-arm units, the x-ray source is collimated so the radiation beam covers the entire fixed detector imaging area or it may be collimated to a smaller size to focus on a region of interest in the object being radiographically imaged, which will use a portion of the detector imaging area. A larger detector is capable of capturing a larger portion of an object in a radiographic image. If a larger or smaller detector were to be installed, the existing collimator may or may not be adaptable to the new size. If a smaller detector were installed, the previously used x-ray beam might overshoot the outside edges of the smaller detector, for example. If a larger detector were to be installed, the aperture of the collimator might not be capable of expanding enough to cover the larger size detector. Another method of addressing these different situations, other than adjusting collimation size, is to move the detector closer to, or further from, the x-ray energy source.

Currently, C-Arms use a motorized telescopic assembly to support and enable the movement of the detector towards the x-ray source. This telescopic assembly (see FIG. 1 #107) may prevent the detector (FIG. 1 #109) from moving as close to the C-arm as desired due to the length required for such a telescopic assembly. In one embodiment, the telescopic assembly may be configured to pass through the C-arm and protrude on the opposite side thereof. Using such a telescopic assembly makes it difficult to position the detector in space constrained areas, such as between a patient's legs, for exams needing horizontal imaging. If the detector can be positioned as close as possible to the C-arm to which it is attached, more distance is made available to move the detector between patient limbs, between physical objects, and into smaller spaces.

The discussion above is merely provided for general background information and is not intended to be used as an aid in determining the scope of the claimed subject matter.

BRIEF DESCRIPTION OF THE INVENTION

A radiographic C-arm system uses a scissor extender assembly to retract and extend a detector in relation to an x-ray source of the C-arm system. The scissor extender assembly is attached to the C-arm near one end of the C-arm. The assembly comprises pivoting arms for extending and retracting the detector away from and toward the x-ray source.

An advantage that may be realized in the practice of some disclosed embodiments of the C-arm radiographic imaging system is easier positioning of the detector end of the C-arm.

In one embodiment, a radiographic C-arm system includes a retractable and extendable support attached to the C-arm, the support comprising pivoting arms for extending and retracting a radiographic system component away from and closer to the C-arm.

In one embodiment, a radiographic C-arm system includes an x-ray source assembly attached to a first end of the C-arm and a retractable and extendable scissor extender attached to a second end of the C-arm. The scissor extender is attached to a detector housing having a digital radiographic (DR) detector secured therein.

In one embodiment, a method of operating a C-arm radiographic imaging system, which comprises an attached x-ray source assembly and an attached digital radiographic (DR) detector, involves attaching the DR detector to a scissor extender having pivoting arms. The C-arm imaging system is positioned about an object to be radiographically imaged, and the DR detector is moved toward the x-ray source assembly by advancing two ends of the pivoting arms toward each other.

A C-arm radiographic imaging system includes a digital detector assembly attached to one end of the arm and an x-ray source assembly attached to another end. The detector assembly includes an electromechanical assembly for positioning the detector close to the C-arm during detector positioning prior to patient imaging, then moving the detector toward the x-ray source, as necessary. An advantage that may be realized in the practice of some disclosed embodiments of the C-arm radiographic imaging system is easier maneuverability of the detector into smaller spaces.

In one embodiment, a C-arm radiographic imaging system includes a processing system and a C shaped arm. An electromechanical assembly attached to the detector includes a scissor extender configured to move the detector closer to or further from the C-arm to which the detector is attached.

In one embodiment, a radiographic imaging system includes a processing system, and a rigid support arm for securing an x-ray source and detector housing in a spatial relationship relative to each other. A detector assembly is attached to a first end of the rigid support arm and includes an electromechanical assembly electrically connected to the processing system. A detector housing is electromechanically attached to the electromechanical assembly. The electromechanical assembly includes a scissors extender to move the detector closer to, or further from, an x-ray source attached to a second end of the rigid support arm.

One embodiment disclosed herein is a digital C-arm radiographic imaging system constructed with a detector housing attached to one end of the C-arm. A detector secured in the housing can be moved toward, and away from, the x-ray source using a scissors mechanism that is extendable and retractable under motorized control. The detector housing may include a detector secured therein and a bracket for attaching the housing to the electromechanical assembly.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

One detector support structure embodiment disclosed herein incorporates pivoting arms, such as in a scissor extender, to replace telescoping elements. The pivoting arms are supported by tracks, motor driven rolling elements, and pivots that allow them to move. A detector housing secures a digital radiographic (DR) detector therewithin and is mounted to the C-arm. When a motor control is used to extend the pivoting arms (FIG. 4A) the arms move the DR detector closer to the x-ray source. When the pivoting arms are collapsed, the DR detector is retracted closer to the C-arm, away from the x-ray source, which creates a compact assembly making it easier to position the DR detector in tight spaces. During this movement of the DR detector, the orientation of the DR detector does not change with respect to the x-ray source.

Figure 1:
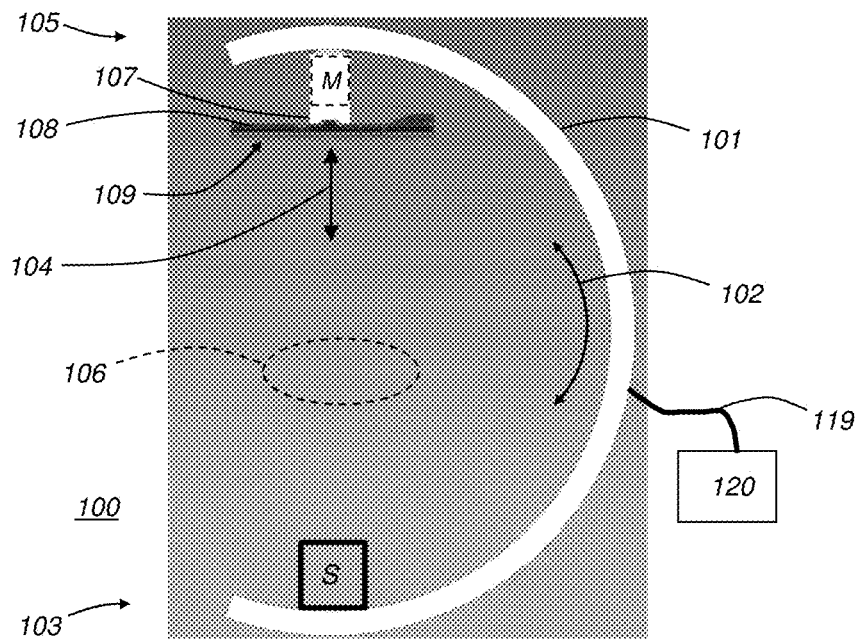
FIG. 1 is a schematic diagram of an exemplary C-arm system.

FIG. 1 is a schematic view of a C-arm x-ray system 100 using a telescopic assembly 107 attached to a detector housing 108 having a detector 109 secured therein. The C-arm system 100 includes a rigid, arc shaped support arm 101 having a first end 103 with an x-ray source assembly S affixed thereto, and a second end 105 having the DR detector 109 attached thereto and configured as described herein. The x-ray source assembly S may include an x-ray source having a remotely controlled collimator, whereby motor driven collimator blades may be moved to control a size and shape of the collimator aperture, and thereby control a size and shape of an emitted x-ray beam. The x-ray source assembly S is fixed in a position to emit an x-ray beam toward the DR detector 109. A patient positioned between the x-ray source assembly S and the DR detector 109 may be exposed by the x-ray source and a radiographic image of the patient may be captured in the DR detector 109. Such a patient is typically lying on a patient bed that is configured to be positioned between the x-ray source assembly S and the DR detector 109, such as in the general region 106. The support arm 101 may be attached to a mobile cart or to a permanent in-room fixture. The support arm 101 is typically configured to be rotatable at least in the directions indicated by the arrow 102, wherein the support arm 101 maintains the relative positions of the detector 109 and x-ray source during rotation. A control system 120 may include a processing system and electronic memory in electrical and digital communication with the x-ray source assembly S, telescopic assembly 107 and DR detector 109 via an electrical and communication cable 119 to carry out programmed instructions and procedures for capturing radiographic images of patients using the mobile C-arm x-ray system 100. The control system 120 may be used to initiate and control firing of the x-ray source in synchrony with an image capture phase of the DR detector 109, for example. Electronic memory in control system 120 may be used to digitally receive radiographic images captured by, and transmitted from, the DR detector 109. The control system 120 may be used to initiate movement of the detector 109 in directions 104 by controlling a motor M in telescopic assembly 107 to extend or retract the detector housing 108 and detector 109.

Figure 2:
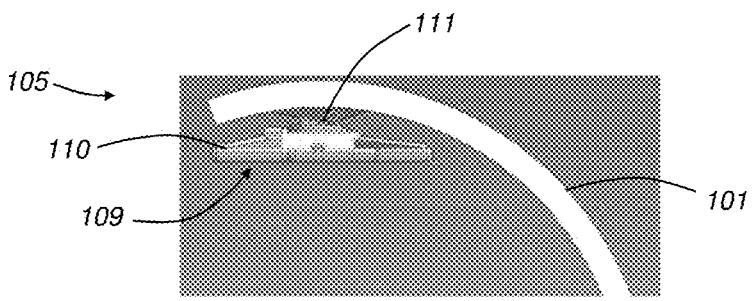
FIG. 2 is a schematic diagram of the detector end of the exemplary C-arm of FIG. 1 showing a new detector assembly.
Figure 3:
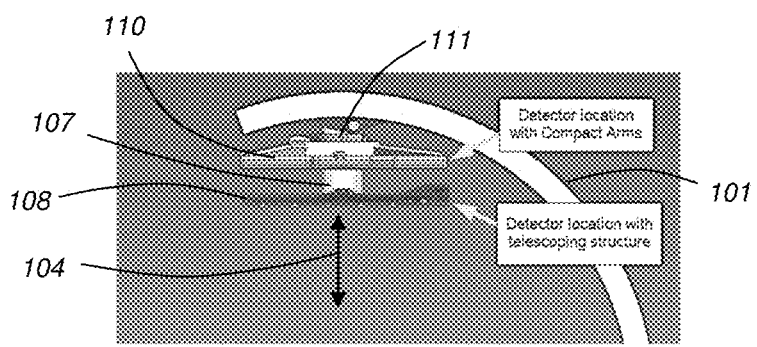
FIG. 3 is a comparison diagram of the exemplary C-arm system and the new detector assembly.

FIG. 2 illustrates another embodiment wherein the second end 105 of the C-arm 101 has a detector housing 110 attached to C-arm 101 with DR detector 109 secured therein, now with a scissor extender assembly 111 attached to the C-arm 101 and to the detector housing 110. As shown, the detector 109 is positioned closer to the C-arm 101, using the scissor extender assembly 111, as compared to the embodiment of FIG. 1 wherein detector 109 is attached to the C-arm 101 using the telescopic assembly 107. FIG. 3 illustrates this comparison whereby the telescopic assembly 107 maintains a distance of the corresponding detector housing 108 further from the C-arm 101 as compared to the detector housing 110 which is attached to the C-arm 101 using scissor extender assembly 111. Both the telescopic assembly 107 and the scissor extender assembly 111 are configured to receive instructions and commands from control system 120 to move the detector 109 in both directions 104.

Figure 4A:
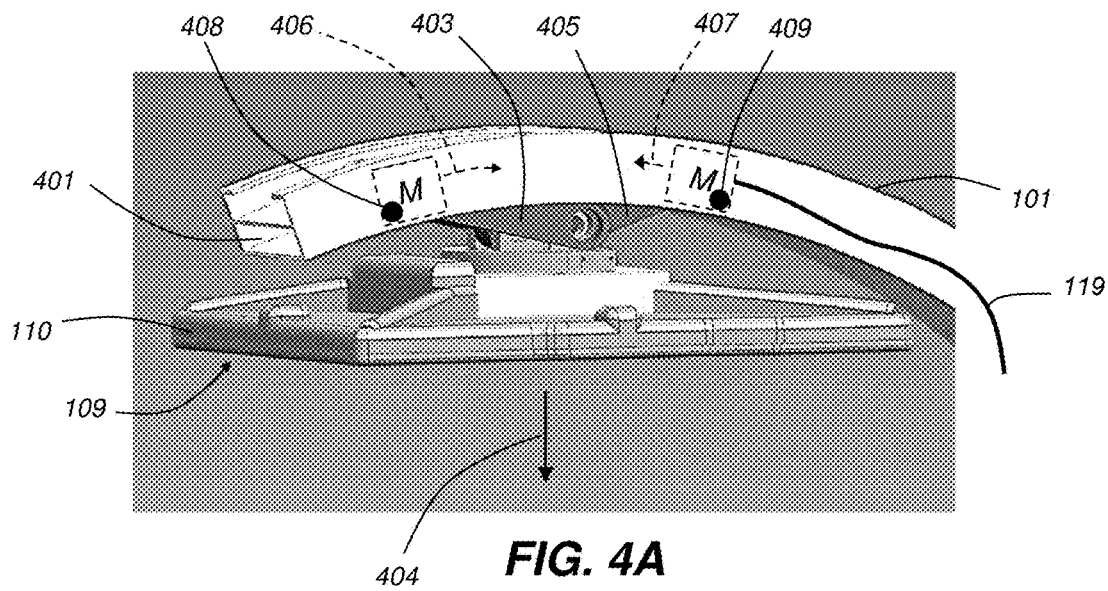
FIGS. 4A-4B are close-up views of the new detector assembly of FIG. 2 in retracted and extended states, respectively.
Figure 4B:
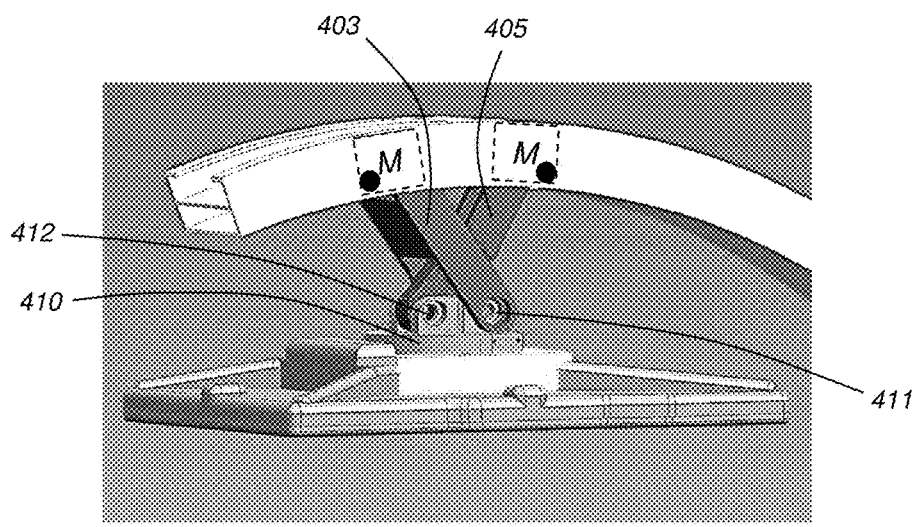

FIGS. 4A-4B illustrate use of the scissor extender assembly 111. Scissor extender assembly 111 includes two pivoting arms 403, 405, each rotatably attached at its lower end to a bracket 412 attached to a top side of the detector housing 110. A pair of rods passing through an opening in each of the pivoting arms 403, 405, and through a corresponding opening 411, 412, in the bracket 410, rotatably secures the pivoting arms to the bracket 410. The upper ends of pivoting arms 403, 405, are each attached to a corresponding motor drive assembly M. The motor drive assemblies M are disposed in a channel, or track, 401 of the C-arm 101. A first motor drive assembly controllably rotates drive wheel 408 in a first direction which, in turn, drives the motor assembly along the track 401, and so moves the attached upper end of pivoting arm 403 in first direction 406. A second motor drive assembly controllably rotates drive wheel 409 in a second direction which, in turn, drives the motor assembly along the track 401, and so moves the upper end of pivoting arm 405 in second direction 407. The pivoting arms may be positioned adjacent to each other or, as shown in FIGS. 4A-4B, one arm 403 may have a forked lower end which straddles the lower end of the other arm 405. Moving the upper ends of the pivoting arms 403, 405, in directions 406, 407, respectively, causes the upper ends of the pivoting arms 403, 405, to converge, or advance toward each other, thereby extending the scissor assembly 111, detector housing 110, and detector 109 secured therein, in direction 404, as shown in FIG. 4B. The motor drive assemblies M may be controlled via command signals received from control system 120, described herein, to move in directions 406, 407, to extend the detector 109 closer to the x-ray source assembly S. The motor drive assemblies M may be controllably moved in an opposite direction to retract the detector housing 110, and detector 109 secured therein, in a direction opposite to direction 404.

Figure 5A:
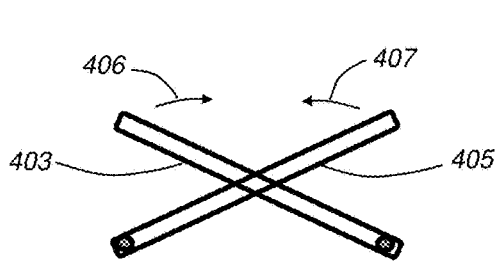
FIGS. 5A-5B are examples of scissor extension embodiments.
Figure 5B:
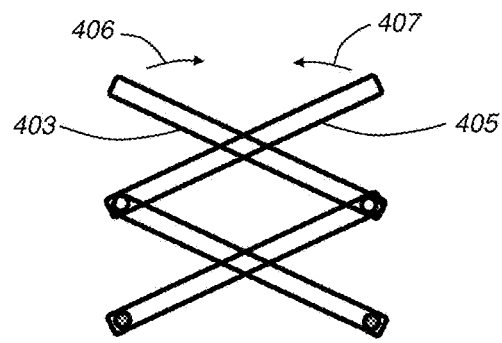

FIG. 5A is a schematic illustration of the geometry of a single stage of the pivoting arms 403, 405, as their upper ends are converging in the directions 406, 407, to extend the scissor extender assembly 111. FIG. 5B is a similar schematic illustration whereby the scissor extender assembly includes two stages, which may be configured for use in the C-arm system 100 to provide a greater extension distance than the single stage embodiment. Similarly, as the upper ends of the pivoting arms 403, 405, are advanced toward each other in directions 406, 407, the two-stage scissor extender assembly is extended.

As will be appreciated by one skilled in the art, aspects of the present invention may be embodied as a system and method. Accordingly, aspects of the present invention may take the form of an entirely hardware embodiment, or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium or electronic memory may be transmitted using any appropriate medium, including but not limited to wireless, wireline, optical fiber, cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to apparatus (systems) and computer programs according to embodiments of the invention. These computer program instructions may be provided to a processor of a general purpose computer, special purpose computer, control system, or other programmable data processing apparatus to produce a machine, such that the instructions or commands, which execute via the processor of the computer or other programmable data processing apparatus, create means for implementing the functions/acts specified.

These computer program instructions may also be stored in a computer readable medium that can direct a computer, other programmable data processing apparatus, or other devices to function in a particular manner, such that the instructions stored in the computer readable medium produce an article of manufacture including instructions which implement the functions.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A radiographic C-arm system comprising:
a C-arm;
a retractable and extendable support attached to the C-arm, the support comprising pivoting arms for extending and retracting a radiographic system component away from and closer to the C-arm,
wherein the support further comprises one of a single stage scissor extender and a multi-stage scissor extender, the support further comprises a motor attached to the scissor extender for extending and retracting the scissor extender, and
wherein the C-arm further comprises a track for guiding the motor along a motor path.

2. The system of claim 1, wherein the support further comprises a plurality of motors configured to controllably converge to controllably extend the scissor extender.

3. The system of claim 2, wherein the track is configured for guiding the plurality of motors along the motor path.

4. A radiographic C-arm system comprising:
a C-arm;
two drive motors configured to drive along a track in the C-arm;
an x-ray source assembly attached to a first end of the C-arm; and
a retractable and extendable scissor extender attached to a second end of the C-arm and attached to a detector housing having a digital radiographic (DR) detector secured therein, wherein the scissor extender comprises pivoting arms for extending and retracting the DR detector away from and closer to the second end of the C-arm, the pivoting arms are each connected to a different one of the two drive motors, and wherein the two drive motors are configured to converge along the track to extend the DR detector away from the second end of the C-arm.

5. The system of claim 4, wherein the two drive motors are configured to diverge along the track for retracting the DR detector closer to the second end of the C-arm.

6. The system of claim 4, wherein the scissor extender comprises one of a single stage scissor extender and a multi-stage scissor extender.

7. A method of operating a C-arm radiographic imaging system which comprises an attached x-ray source assembly and an attached digital radiographic (DR) detector, the method comprising:
attaching the DR detector to a scissor extender, the scissor extender comprising two pivoting arms;
attaching two motors to the scissor extender, each of the two motors attached to a different one of the two pivoting arms, and configuring each of the two motors to travel along a track in a C-arm of the C-arm radiographic imaging system;
positioning the C-arm imaging system about an object to be radiographically imaged; and
adjusting a position of the DR detector relative to the x-ray source assembly comprising advancing two ends of the pivoting arms toward or away from each other by driving the two motors along the track in the C-arm.

8. The method of claim 7, wherein the step of attaching the DR detector to a scissor extender comprises attaching the DR detector to a multi-stage scissor extender.

* * * * *